United States Patent [19]

Gunasingham

[11] Patent Number: 5,312,590
[45] Date of Patent: May 17, 1994

[54] AMPEROMETRIC SENSOR FOR SINGLE AND MULTICOMPONENT ANALYSIS

[75] Inventor: Hari Gunasingham, Singapore, Singapore

[73] Assignee: National University of Singapore, Kent Ridge, Singapore

[21] Appl. No.: 342,075

[22] Filed: Apr. 24, 1989

[51] Int. Cl.$^5$ .............................. G01N 27/12
[52] U.S. Cl. .................... 422/56; 422/82.02; 422/82.03; 422/98; 435/11; 435/14; 435/817; 204/403
[58] Field of Search ............ 422/56, 57, 82.01, 82.02, 422/82.03, 98; 435/817, 11, 14; 204/403

[56] References Cited

U.S. PATENT DOCUMENTS

| | | | |
|---|---|---|---|
| 4,225,410 | 9/1980 | Pace | 422/98 X |
| 4,517,291 | 5/1985 | Seago | 435/817 X |
| 4,525,265 | 6/1985 | Abe et al. | 435/817 X |
| 4,545,382 | 10/1985 | Higgins et al. | 204/403 X |
| 4,871,440 | 10/1989 | Nagata et al. | 435/817 X |

FOREIGN PATENT DOCUMENTS 0127958 12/1984 European Pat. Off.
0136362 4/1985 European Pat. Off.

OTHER PUBLICATIONS

Henning et al., J. Am. Chem. Soc., 104, 5862-5868 (1982).

Primary Examiner—James C. Housel
Assistant Examiner—Jeffrey R. Snay
Attorney, Agent, or Firm—Gregory O. Garmong

[57] ABSTRACT

A device for detecting chemical species in liquids having one or more sensor elements is described. Each sensor element includes a test electrode coated with a perfluorinated ion-exchange polymer film incorporating a redox mediator; an immobilized enzyme layer and, over this, a semipermeable membrane. The invention discloses the method whereby the test electrode is normally kept at a zero potential and then poised at a positive potential for a few milliseconds during which time the test signal is evaluated. The invention formulates a method for calibrating each measurement sample and reference solution wells. These are symetrically arranged with respect to the sensor element so that the center of the sample solution well and the center of the reference solution well are equidistant to the sensor element. Thus the diffusion of chemical species from the sample and reference solutions occurs equally and can be correlated. The invention additionally discloses a method for selectively detecting a number of species in a single sample drop through the provision of multi-sensor elements. The technique proposed in the invention is particularly suitable for the determination of glucose and cholesterol in biological fluids.

13 Claims, 5 Drawing Sheets

AMPEROMETRIC SENSOR FOR SINGLE AND MULTICOMPONENT ANALYSIS

BACKGROUND OF THE INVENTION

This invention relates to a method for the analysis of chemicals in liquids. This is accomplished by means of a dry chemistry test device made up of one or more selective amperometric sensor elements coated with specific chemical reagent layers and an electronic apparatus that provides a pulse measurement voltage to the sensors.

The analysis of chemical species in liquids can be carried out by wet chemistry or by dry chemistry systems. Wet chemistry analyses employ reagents in liquid solution and are widely used in both manual and automated analytical methods. In dry chemistry systems, a complete chemistry for a particular analysis is miniaturized into a single test probe or device. No prior reconstitution of reagents is required. The dry chemistry methods are often simpler in design, require less reagent manipulation, give quicker results and are more stable. These advantages coupled to the feasibility of using small instrumentation favours more decentralized clinical testing.

In a U.S. Pat. No. 4,042,335 issues to Clement on Aug. 16, 1977, a multilayered test device for the analysis of liquids is described. The device includes a reaction layer including a composition that is interactive in the presence of a predetermined analyte to provide a diffusable detectable species, and a registration layer that is permeable to the detectable species and within which the species can be detected by diffuse reflectance spectroscopy. The element can include other layers which provide for radiation blocking and for uniform spreading of the test sample.

Dry chemistry systems can be defined as disposable, single-use devices or multi-use devices, depending on whether the analytical reaction occurring in the reaction layer is reversible.

Dry chemistry tests based on enzyme-catalysed reactions have become widely used. By way of example are dry chemistry test devices for the measurement of glucose in blood developed by Boehringer Mannheim Corporation. The device is a flat strip that employs a reaction layer consisting of glucose oxidase-peroxidase enzymes coupled to a redox mediator dye. The reaction layer is supported in a inert film carrier matrix. The blood sample is analysed by placing about 50 ul of whole blood on the surface of the dry chemistry strip. The plasma containing the glucose is separated from the red blood cells by the carrier matrix. After about 1-3 minutes, the red blood cells are removed by washing or wiping and the colour developed is measured by reflectance spectroscopy. In a similar device developed by Ames Division, Miles Laboratories Inc., a separate film membrane is placed over the carrier matrix to separate the red blood cells.

Electrochemical dry chemistry enzyme test devices have been developed as an alternative to spectrophotometric devices. These include amperometric and potentiometric devices. Electrochemical systems have the advantage that they can be used as disposable, single-use devices as well as multiple-use devices in continuous-flow and automated systems.

Amperometric dry chemistry enzyme test devices include a sensing element comprising a measuring or working electrode and reference electrode. The electrodes are coated with an enzyme and optional mediator and, over this, a membrane to prevent interfering species from reacting at the measuring electrode. When an appropriate test potential is applied, the measuring electrode provides a faradaic current proportional to the concentration of the chemical species being determined.

As an example of prior art in this field, U.S. Pat. No. 3,539,455 issued to Clark in Nov. 1970 discloses an amperometric dry chemistry device based on glucose oxidase suitable for the determination of glucose.

The role of the redox mediator is to serve as an electron shuttle between the active center of the enzyme and the electrode. Various redox mediators have been used in enzyme electrodes. For example, an article published in Clinica Chimica Acta in 1974 describes a range of mediators which include ferricyanide, quinones and organic dyes. European patent application EP 0,136,362,A1 published on 04 Oct. 1985 describes an amperometric test device for monitoring blood-glucose levels comprising a measuring electrode and reference electrode coated with a porous support carrying glucose oxidase and a redox mediator, and over this, a membrane to prevent interfering molecules from reacting at the measuring electrode.

Higgins et. al. have described the use of ferrocenes as a mediator for glucose oxidase-based enzyme sensor for glucose in European patent application EP 0,127,958,A2 published on Dec. 12, 1984; U.S. Pat. No. 4,545,382 dated Oct. 8, 1985; and U.S. Pat. No. 4,711,245 dated Dec. 8, 1987. Another mediator system employs organic metal coatings based on salts of tetracyanoqunidimethane as first described by Cenas and Kulys, Bioelectrochem Bionerg. 8(1981)103 Albery has filed an application based on this work in European patent application EP 0,184,909,A2. Albery et. al. have also shown that tetrathiafulvalene can act as a mediator for glucose oxidase in the determination of glucose ( W.J. Albery, P.N. Bartlett and D.H. Craston, J. Electroanalytical Chemistry, 194(1985)223).

Although spectrophotometric and amperometric dry chemistry test devices are gaining increasing usage, present systems suffer from a number of practical limitations.

First, in the case of disposable single-use dry chemistry test devices, it is not possible to calibrate every measurement. Presently the practice is only to calibrate every batch by means of a two point calibration using test devices representative of the batch. It is then assumed that the calibration holds for the remaining devices in the batch. The difficulty that arises is that there is no way of knowing if any of the remaining devices are defective for whatever reason.

A further consideration is that, because the measurement of chemical species in blood is sensitive to the blood matrix, it is necessary to use reference calibrators that mimic the average human blood matrix as close as possible. The need for calibration is even greater for amperometric devices where changes in the electrode response characteristics can occur for a number of reasons.

Further, single use test devices, especially for blood-glucose monitoring are often intended for home care applications where the user is generally not highly skilled or trained. Consequently, poor analytical results may be obtained where the user technique is incorrect or where the test devices have been badly handled or stored in adverse conditions.

Second, present disposable, single-use test devices normally can determine only one chemical species. Thus, if several different analyte in a particular sample have to be determined, multiple samples have to be obtained and a different sensor must be used used for each analyte. This is time consuming, requires extra manipulation and is expensive.

Third, in present systems because of the requirement that all devices in a batch must be identical, the manufacturing and quality control process must be quite stringent increasing the cost of production. Again this is more difficult to achieve for dry chemistry devices based on amperometric sensing.

Fourth, redox mediators that are commonly used in amperometric glucose-oxidase based sensors have increased solubility in the active, oxidised form. Thus, when the sensor is continuously poised at a positive operating potential in multiple-use applications, loss of mediator in the oxidised form occurs readily from the electrode surface. This leads to a loss of sensitivity and a limitation in the linear range with time.

Fifth, even though the use of a redox mediator enables the operating potential to be reduced by several hundred millivolts, significant interference from electroactive species such as ascorbic acid is still found. For some cases the mediator can actually enhance the signal due to the interfering species. This leads to erroneous results that can have serious clinical consequences.

Because of these problems, previous approaches to enhancing the performance of amperometric dry chemistry enzyme test devices have not been entirely successful.

Accordingly, it is an object of the present invention to provide a general amperometric dry chemistry enzyme test device for measuring chemical species such as glucose and cholesterol in liquids.

It is another object of the present invention to provide a method for measuring glucose concentrations in liquids using the enzyme glucose oxidase.

It is a further object of the present invention to provide a method for measuring chemical species such as glucose and cholesterol in liquids by providing a means for calibrating the test device for each measurement.

Yet another object of the invention is to provide a method for measuring chemical species such as glucose and cholesterol in liquids using a test device having multiple sensors to simultaneously measure more than one chemical species.

Still, a further object of the present invention is to provide a method for measuring chemical species such as glucose and cholesterol in liquids using a selective sensor element comprising an electrode system coated with an perfluorinated cation exchange polymer film incorporating a redox mediator.

Yet another object of the present invention is to provide a method for measuring chemical species such as glucose and cholesterol in liquids using a pulse detection mode to minimise loss of the mediator and enable reactivation of the sensor electrode.

Still other objects of the invention will in part be obvious, and will, in part, be apparent from the following description.

SUMMARY OF THE INVENTION

This invention relates to a method and apparatus for measuring a wide range of chemical species in liquids. In its general embodiment it employs a flat test device comprising a number of symmetrically arranged sensor elements that enable multi-species determination from a single sample drop. Each sensor element is coated with a unique reaction layer that makes it responsive to specific chemical species. Additionally, all the sensor elements are coated with a single membrane which serves the dual function of a diffusion barrier and filter. An insulating layer is further coated over the membrane with specific provision for wells where the sample and reference solutions may be placed. According to the preferred form of the invention, the sample well is centrally located so that chemical species present in the sample can diffuse equally to the various sensing elements. The reference solution wells are located adjacent to the specific sensing element The center of the sample solution well and the center of the reference solution well are equidistant to the respective sensing element so that the diffusion of chemical species from the sample and reference solutions occurs equally.

According to one preferred form of the invention, the sensing element comprises a working electrode and reference electrode. The working electrode can be made of carbon paste, platinum or gold whereas the reference electrode is made of silver coated with a silver chloride layer. The reference electrode can alternatively be made of carbon, gold or platinum. The working electrode is coated with a reaction layer consting of an enzyme specific to the chemical species being detected. An optional redox mediator can be included in the reaction layer to take the place of the naturally occurring oxygen to transfer electrons from the enzyme to the electrode.

In the case a mediator is used, it is preferable to have it incorporated into an perfluorinated ion exchange polymer film that is coated on the test electrode. The ion exchange polymer is preferably a copolymer of tetrafluorethylene and perfluoro [2-(fluorosulfonylethoxy) propylvinyl ether manufactured by E.I. du Punt Nemours & Co. Inc commonly referred to by its trademark, Nafion. This polymer combines the hydrophobic properties of its Teflon backbone with the superacidity and selective permeability of sulfonic acid functional groups. The key property of Nafion that is exploited in this invention is the fact that the polymer is permeable to cations but is impermeable to anions and nonpolar compounds. Thus it is able to exclude anionic interferences such as that of ascorbic acid and paracetamol.

Whereas various mediator compounds can be used in accordance with the invention, the preferred form of mediator is tetrathiafulvalene (2,2'-bi-1,3-dithiole) or its derivatives.

The tetrathiafulvalene (TF)- Nafion system provides a unique mediator system whereby the selectivity of the sensor element is enhanced and electrode fouling minimised. Also, the stability of the sensing element is enhanced because of the ability of Nafion to selectively bind positively charged, oxidised forms of TTF. The TTF-Nafion matrix also provides a medium for ionic conduction as well as electronic conduction which further improves the performance of the sensor.

Another aspect of the present invention therefore is a method of using the TTF-ion exchange polymer as a redox mediator system for enzyme reactions.

According to another form of the invention, the sensing element can utilise a third electrode in addition to the working and reference electrode. The purpose of the third electrode is provide improved potential control where a potentiostat is used.

The enzyme system used depends on the chemical species that is to be detected. It can be selected from a range of flavoproteins which include glucose oxidase and haem-containing enzymes such as horseradish peroxidase. Horseradish peroxidase can be used in conjunction with other hydrogen peroxide generating enzymes such as cholesterol oxidase.

Another aspect of the invention relates to the use of a pulse detection mode whereby the test electrode is normally kept at zero potential. The test signal is then only evaluated during the few milliseconds that the electrode is poised at the positive test potential. By doing this it is possible to minimize the loss of mediator, enhance the electrocatalytic performance and increase the linear range.

The invention also relates to a measurement apparatus comprising an electronic circuit for applying predetermined pulse potential sequence to each sensing element and a multiplexed current-to-voltage converter that enables the monitoring of the current derived from each sensing element in a specified sequence whereby the sample and reference values can be differentiated. A microprocessor is used to direct the actual sequence and it also records the current in digital form and converts this into concentration units by comparison with values obtained for the reference solutions either by a standard addition method (where a single reference solution is used) or by a two point calibration (where two reference solutions are used).

A presently preferred use and application of the invention is the measurement of chemical species such as glucose and cholesterol in physiological fluids such as blood and urine. In blood-glucose analysis a sample drop as small as 10 ul can be used. The analysis is done automatically in a specific sequence under the control of the microprocessor.

A key advantage of the invention is that by virtue of the ability to calibrate each measurement it is feasible to ensure a high level of accuracy.

In accordance with the invention a method of measuring chemical species in liquids is provided. The method includes steps of i) fabricating a dry chemistry amperometric test device comprising one or more sensor elements each coated with a redox mediator/ion exchange polymer film, enzyme and semipermeable membrane ii) providing a pulse mode of detection and iii) providing a means of calibrating every measurement. The invention can be seen as a marked improvement over existing amperometric sensors for both single use and multi-use applications. The sensor system has particular application to the measurement of chemical species such as glucose and cholesterol in biological fluids. Further, the system enables multi-species measurements using a single strip and a single sample drop of less than 10 ul. The system can be used for home monitoring as well as in the hospital and doctors clinic.

The nature of the invention is further illustrated in the drawing in which:

FIG. 6 is a perspective exploded view (FIG. 6(a) and plan views of the individual layers (FIGS. 6(b)–6(e)) amperometric dry test strip for multi-species detection FIG. 7. is a view of a flow cell (FIG. 7(a)) and its associated test device (FIG. 7(b)) used for continuous-flow analysis.

FIG. 8 shows a calibration plot (FIG. 8(a)) for successive injections of varying concentrations of glucose using the the flow cell of FIG. 7 and glucose enzyme test device described in FIG. 3, using the flow injection profiles shown in FIG. 8(b).

FIG. 9 is a block diagram of an electronic apparatus according to one embodiment of the system.

DESCRIPTION OF THE PREFERRED EMBODIMENTS

EXAMPLE 1

Nafion-Tetrathiafulvalene Mediator System

Figure 1:
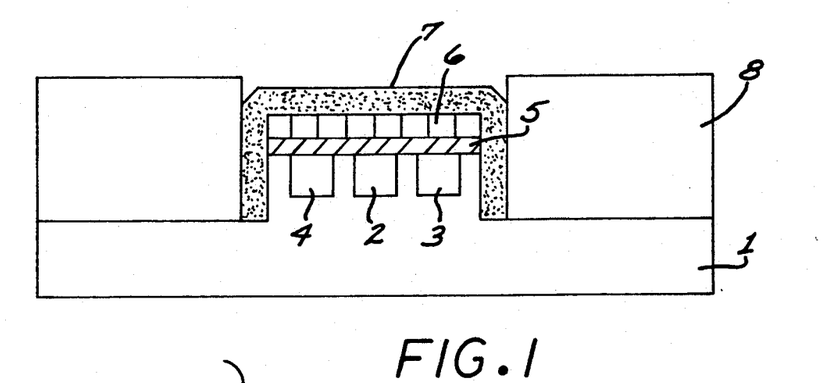
FIG. 1 is a schematic diagram showing the glucose sensor element.

A sensor element according to one form of the invention that is selectively responsive to glucose is shown in FIG. 1. The base of the sensor (1) is made of an inert plastic such as teflon. The measuring (2), counter (3) and reference (4) electrodes are embedded in the plastic so that the surfaces of the electrodes are flush with the plastic base. The measuring (2) and counter (3) electrodes are made of graphite whereas the reference electrode (4) is made of silver. The silver surface is coated with silver chloride.

At least one of the working electrode (2) and the counter electrode (3) may be made by screen printing carbon ink onto the base strip (1). At least one of the working electrode (2) and the counter electrode (3) may be made by screen printing a metallo-organic liquid onto the base strip (1), which in this case is made of glass or ceramic, and then fired. The working electrode (2) may be made of gold or platinum, in the form of a microelectrode array formed on a substrate made of glass or silicon. The microelectrode is prepared by photolithographic technique.

The base electrodes are then coated with three distinct chemical layers: The first coating over the electrodes (5) consists of a film of Nafion incorporating tetrathiafulvalene (TTF). This is formed by droplet evaporating 10 ul of a 5% by weight ethanolic Nafion solution. The TTF is preferably incorporated into the Nafion film in such a way as to ensure a uniform distribution in the film.

A preferred approach is to immerse the Nafion ion exchange polymer film coated electrode in an aqueous solution of 1 mM TTFCl for 10 minutes as described by Henning et. al. (J. American Chemical Society, 104(1982)5862–5868). The Nafion film turned a golden colour after immersion in the TTF+ solution due to the incorporation of TTF according to the following scheme:

Further treatment of the TTF-Nafion electrode may be done by potential cycling in an 1.0 M KBr solution which leads to the formation of zones of TTF-Br crystals. Electrocrystallisation can be similarly carried out to form TTF-I and TTF-BF$_4$ crystals. These TTF crystals grow three dimensionally and are electronically conducting, thus facilitating electronic conduction through the Nafion film. Thus the TTF-Nafion film is unique as it provides electronic conduction as well as ionic conduction.

The enzyme layer (6) is next deposited by placing 10 ul 2% glucose oxidase (EC 1.1.3.4 Type II from Aspergillus Niger) made up in 0.1 M pH 7.4 sodium phosphate buffer containing 0.01% w/v sodium azide over the Nafion/TTF layer. The enzyme was dried overnight at 4° C. 5 ul of a freshly prepared 1:1 mixture of 10% bovine serum albumin ( Fraction V 96–99% Albumin) and 2.5% gluteraldehyde was then placed over the dried enzyme layer covered by a 0.03 micron pore size polycarbonate membrane (7). The enzyme may also be a mixture of cholesterol oxidase, chloresterol esterase, and horseradish peroxidase, so that the sensor is selective to total cholesterol. The membrane may also be made of cellulose acetate, polyvinyl alcohol, or polyurethane. The test device was allowed to dry overnight at 4° C. The entire assembly was held in place by means of the plastic cover (8).

In place of the polycarbonate membrane, a cellulose acetate or cellulose nitrate membrane can be employed. In this case the membrane is formed by dip coating the sensor in a 1% w/v solution of the cellulose acetate or cellulose nitrate in a acetone/cyclhexanone mixture.

Figure 2:
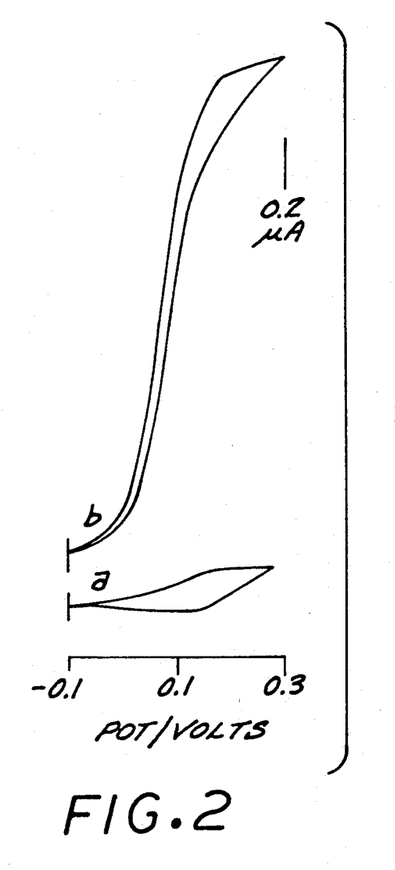
FIG. 2 shows the current potential response of the glucose sensor element shown in FIG. 1 in the absence and presence of glucose.

The interaction between the TTF/Nafion mediator and glucose oxidase was investigated by DC cyclic voltammetry. FIG. 2a shows a typical cyclic voltammogram obtained for the TTF/Nafion system in a phosphate buffer solution of pH 7.4 . On addition of 20 mM glucose the cyclic voltammogram ( FIG. 2b) shows a large anodic catalytic current due to the regeneration of the reduced form of the mediator by the immobilized glucose oxidase.

EXAMPLE 2

Pulse mode of detection

The glucose sensor shown in FIG. 1 was operated in the pulse potential mode in which the working electrode is pulsed between OV and + 150 mV with respect to the silver-silver chloride reference electrode. The duration at OV ranges between 300 and 500 milliseconds, whereas the duration at +150 mV ranges between 50 and 60 milliseconds.

At OV, the TTF in the Nafion film is in the reduced form. The catalytic current response is thus only obtained when the working electrode poised at +150 when the TTF is oxidised to TTF+. The test measurement is made 10 milliseconds before the end of the positive pulse to allow the working electrode capacitive charging current to decay.

EXAMPLE 3

Two point calibration

Figure 3:
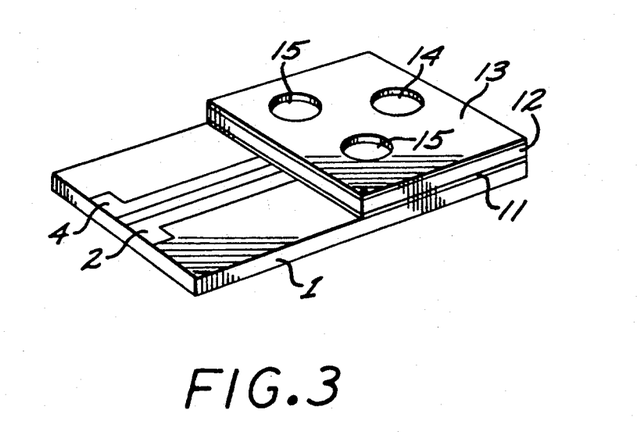
FIG. 3 is a schematic diagram of the amperometric dry chemistry test device for single species analysis which can be used for glucose determination.

FIG. 3 shows a schematic diagram of an amperometric dry chemistry test device for glucose measurement that has specific provision for reference solution wells in addition to the sample well that enables either a two point or one point calibration. In this device only a measuring (2), and reference (4) electrodes are employed.

The electrodes are coated with the Nafion-TTF-Glucose oxidase reaction reaction layer (11) and membrane layer (12) as described in Example 1. Next an insulating layer (13 is placed over the membrane layer with provision for sample (14) and reference (15) wells.

The wells are symmetrically arranged in relation to the electrodes so that the center point of each well is equidistant to the center point of the measuring electrode (2). In an actual analysis, the reference and sample solutions are measured by placing a drop of the solution in the respective well while the pulse potential is applied to the working electrode. A specific sequence is followed: First the low reference solution is measured, then the sample solution is measured and then the high reference solution is measured.

Figure 4:
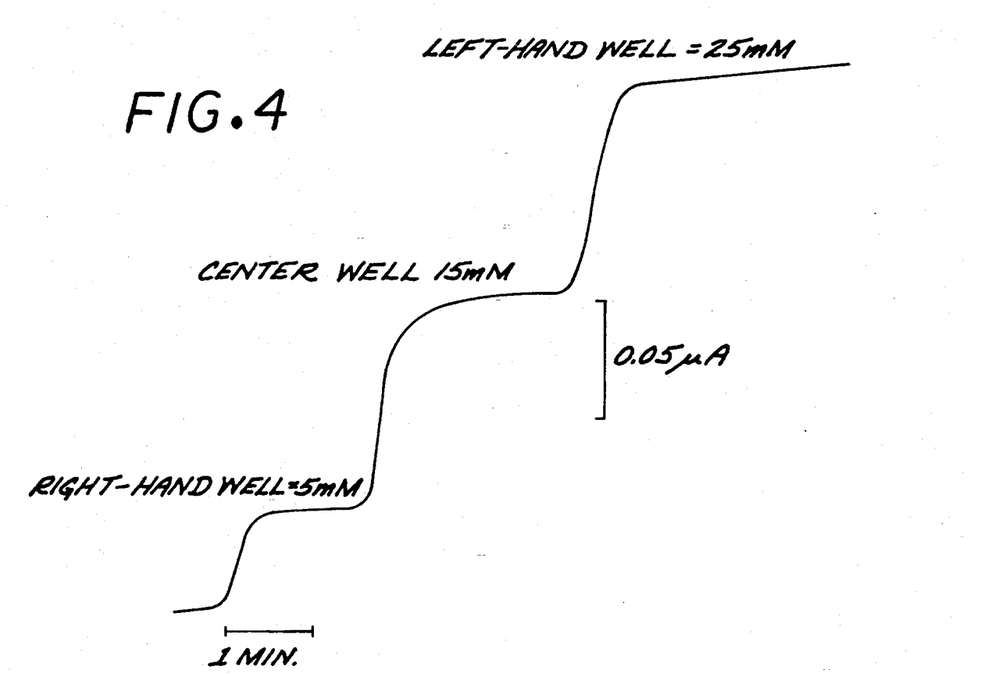
FIG. 4 shows the response of the amperometric test device shown in FIG. 3 for the sequential addition of low, medium and high glucose standards.
Figure 5:
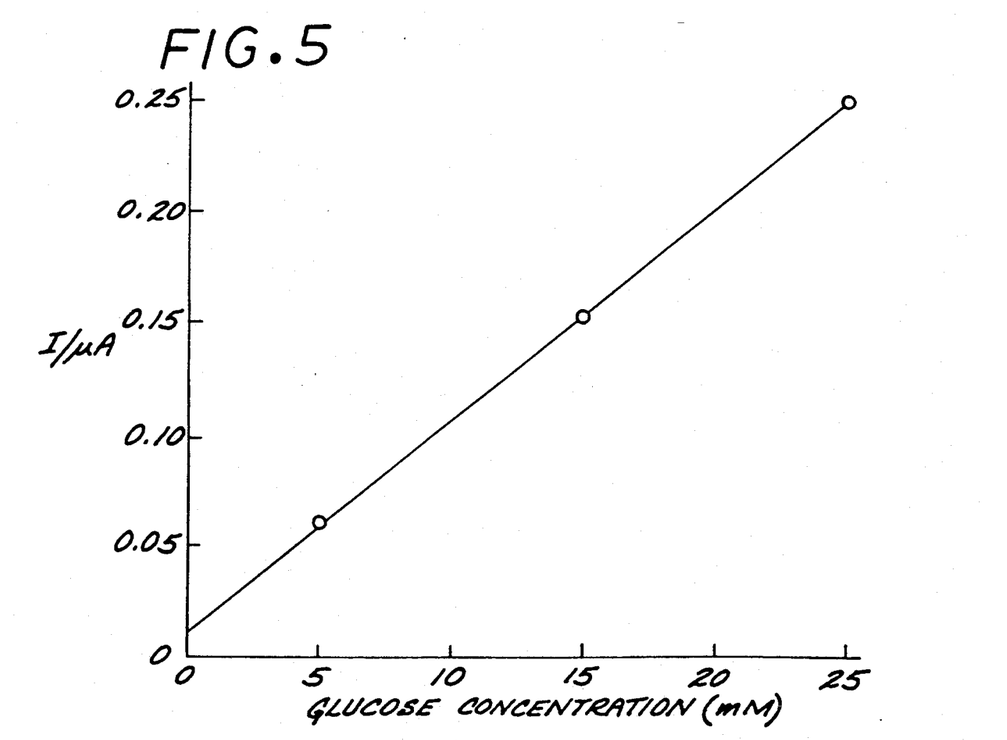
FIG. 5 shows a calibration plot derived from the response curves shown in FIG. 4.
Figure 6A:
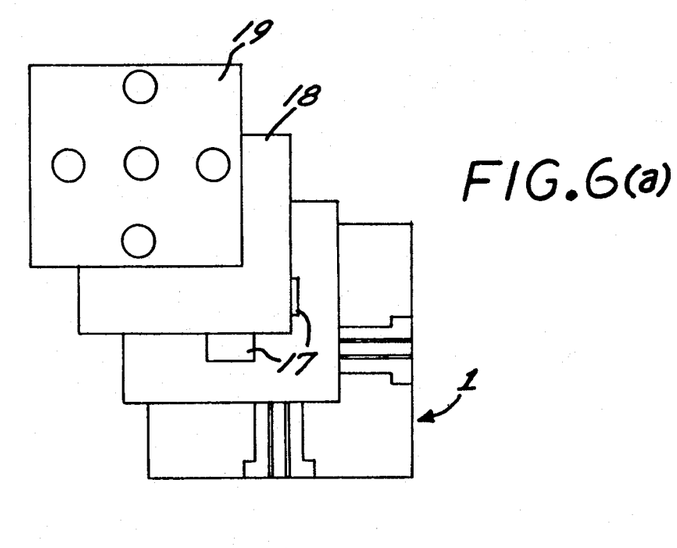
Figure 6B:
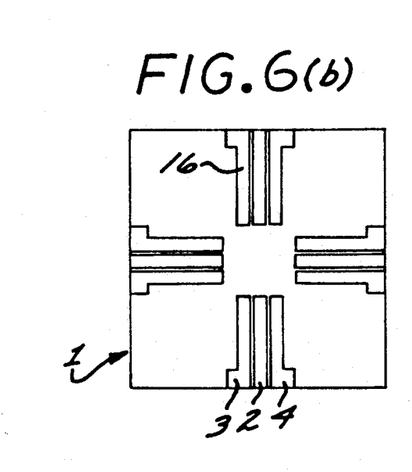
Figure 6C:
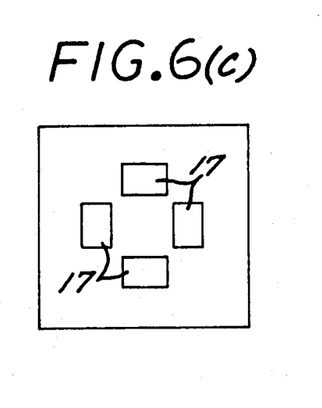
Figure 6D:
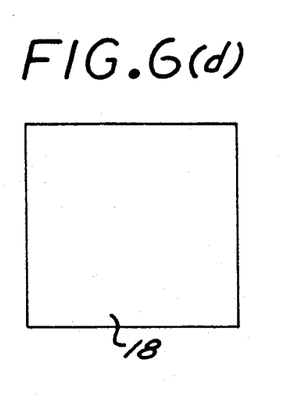
Figure 6E:
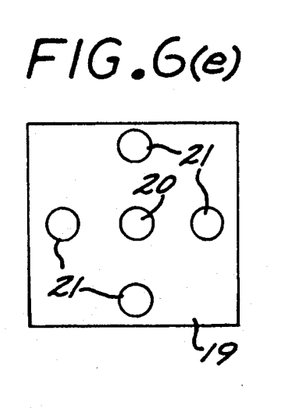

FIG. 4 shows the current response of the device during an actual analysis and FIG. 5 gives a calibration plot which shows the response to be linear.

It will be obvious from the above example that a one point calibration can be performed using a single reference solution.

EXAMPLE 4

Multi-Species Detection

A dry chemistry test device for multi-species detection is shown in FIG. 6 which gives an exploded view of the device. The device consists of four symmetrically arranged sensor elements (16) that enable multi-species determination from a single sample drop. Each sensor element is coated with a unique reaction layer (17) that makes it responsive to specific chemical species. Additionally, all the sensor elements are coated with a single membrane (18) which serves the dual function of a diffusion barrier and filter. An insulating layer (19) is further coated over the membrane with specific provision for wells where the sample (20) and reference solutions (21) may be placed. The sample well is centrally located so that chemical species present in the sample can diffuse equally to the various sensing elements. The reference solution wells are located adjacent to the specific sensing element. The center of the sample solution well and the center of the reference solution well are equidistant to the respective sensing element so that the diffusion of chemical species from the sample and reference solutions occurs equally.

EXAMPLE 5

Continuous-flow monitoring

In another form of the invention, the dry chemistry device can be used for automated, continuous-flow monitoring. For this purpose use is made of a flow cell as described in FIG. 7.

In this flow cell, the dry chemistry test device (22) employed. The inlet (23) is placed directly opposite the central sample well (24) of the test device. The outlet (25) determines the level of the cell solution reservoir (26). The flow cell may have an inlet placed opposite a sample well, the inlet having a diameter of 0.3 to 0.5 millimeters and a distance from the sample well of 1 to 2 millimeters, and an outlet positioned to control the level of the solution in the cell reservoir. Although the diameter of the inlet is variable, the preferred diameter is 0.3 mm. The preferred distance between the inlet and test device is 1 mm.

A key feature of the flow cell design is the fact that the test device can be easily positioned and the fact that there is no need to enclose the cell to prevent leakages as in conventional designs.

The flow cell is usually operated in a flow-injection mode where a discrete volume of the sample (usually between 10 to 100 microliters) is injected into the cell to give a transient peak shaped response. The peak height is proportional to the concentration of the chemical species being measured.

Figure 8A:
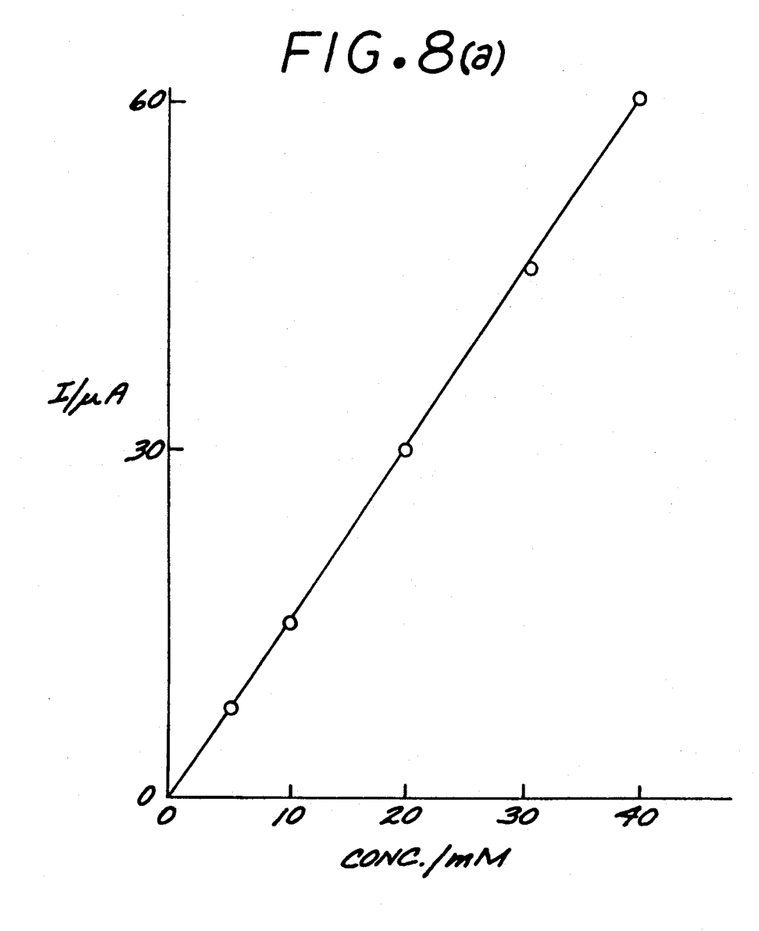
Figure 8B:
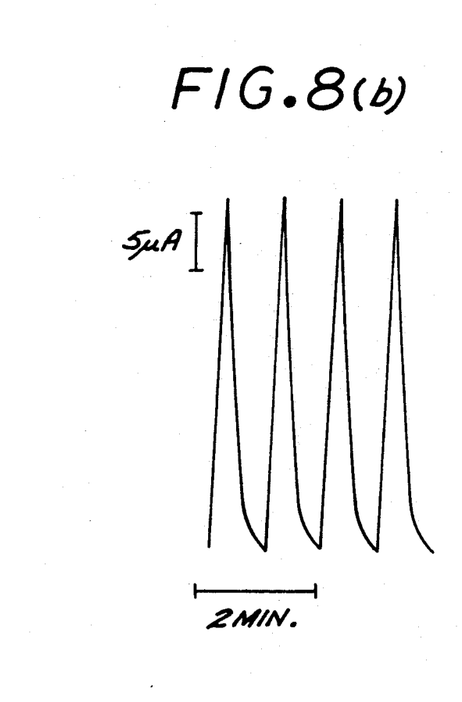

FIG. 8 shows the actual flow-injection profiles and the corresponding calibration plot for successive injections of various concentrations of glucose standards. It can be seen that the plot is linear up to glucose concentrations of 40 mM.

EXAMPLE 6

Instrumentation

Figures 7A, 7B, 9:
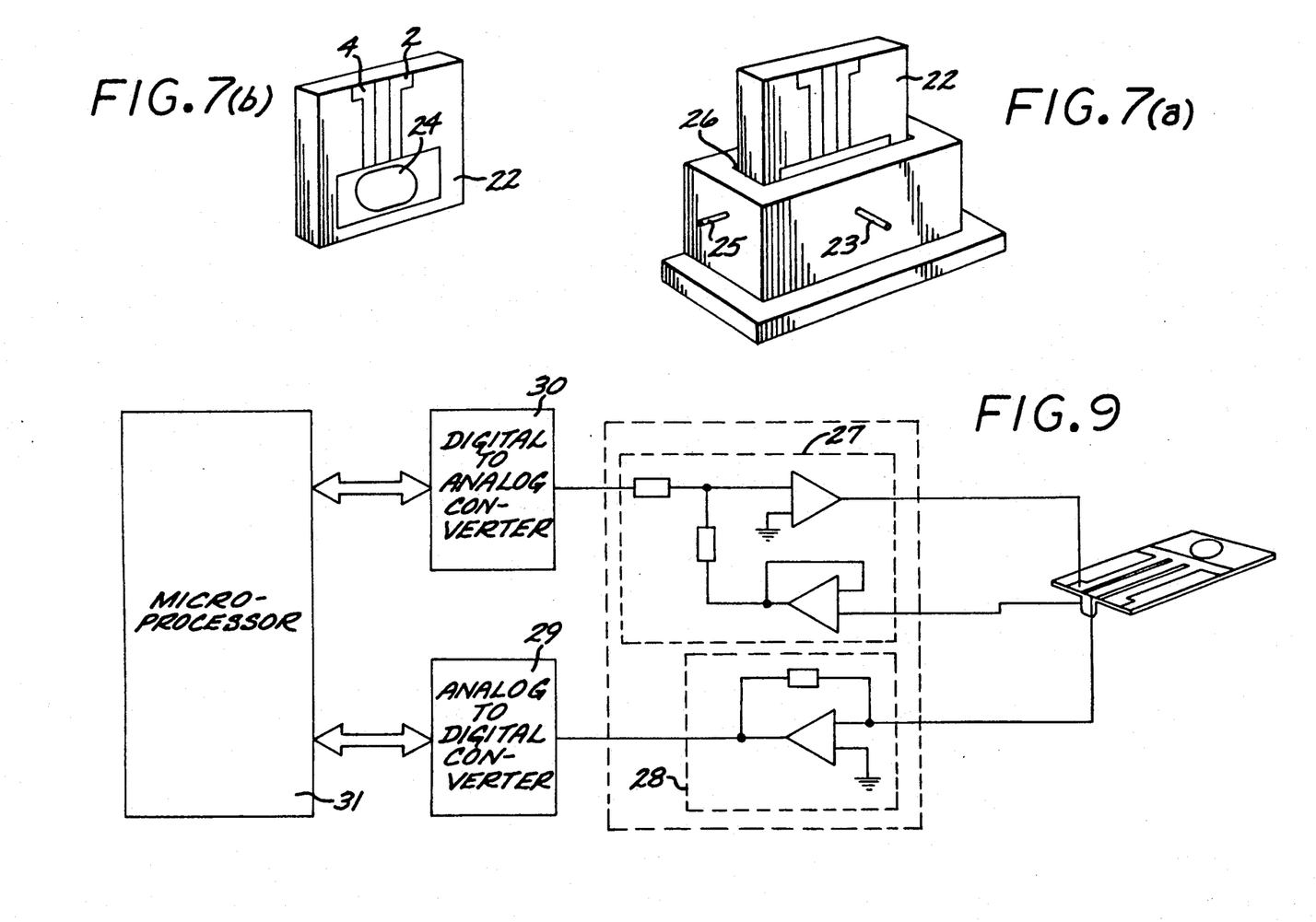

The microprocessor-based instrumentation for the control of the amperometric dry chemistry test devices is described in FIG. 9. The instrumentation comprises a potentiostat (27), sensitive current monitor (28), analog-to-digital converter (29), digital-to-analog converter (30) and microprocessor (31).

Pulse waveforms for the pulse mode of detection is conveniently generated by the microprocessor software through the digital-to-analog converter (30). The test current can be sampled via the analog-to-digital converter (29).

What is claimed is:

1. An amperometric dry chemistry test apparatus applicable to a broad range of chemical analyses, comprising:
    a dry-chemical test device including
        a bottom layer of a non-conducting material having at least two working electrode/reference electrode pairs supported by the non-conducting material with a face of each electrode exposed at a surface of the bottom layer;
        a second layer overlying the bottom layer including aperfluorinated ion exchange film incorporating a redoxmediator overlying the bottom layer and the electrodes, and an enzyme-containing layer overlying the ion exchange film,
        a third layer overlying the second layer comprising a permeable membrane, and
        a top insulating layer overlying the third layer with separate wells for a sample and for a reference standard therein, the top insulating layer having at least one sample well and at least one reference well adjacent each working electrode/reference electrode pair, the distance from each of said at least one sample well to said adjacent working electrode/reference electrode pair being substantially the same as the distance from each said at least one reference well to that same working electrode/reference electrode pair; and
    a microprocessor-based measuring apparatus operatively connected to the working electrode/reference electrode pairs.

2. An amperometric dry chemistry test apparatus applicable to a broad range of chemical analyses, wherein the apparatus is used to analyze several chemical species from a single sample drop of less than 10 microliters volume, comprising:
    a dry-chemistry test device including
        a bottom layer of a non-conducting material having at least two working electrode/reference electrode pairs supported by the non-conducting material with a face of each electrode exposed at a surface of the bottom layer,
        a second layer overlying the bottom layer including a perfluorinated ion exchange film incorporating a redox mediator overlying the bottom layer and the electrodes, and an enzyme-containing layer overlaying the ion exchange film,
        a third layer overlying the second layer comprising a permeable membrane, and
        a top insulating layer overlying the third layer with separate wells for a sample and for a reference standard therein, the top insulating layer having a sample well for the sample drop and at least one reference well adjacent each working electrode/reference electrode pair, the distance from the sample well to said adjacent working electrode/reference electrode pair being substantially the same as the distance from each said at least one reference well to that same working electrode/reference electrode pair; and
    a microprocessor-based measuring apparatus operatively connected to the working electrode/reference electrode pairs.

3. The test apparatus of claim 2, wherein
    each working electrode is made of a material selected from the group consisting of carbon, gold, and platinum, and
    each reference electrode is made of a material selected from the group consisting of carbon, gold, and platinum.

4. The test apparatus of claim 2, wherein each working electrode is made of a material selected from the group consisting of gold and platinum, and each working electrode is a microelectrode array formed on a substrate made of a material selected from the group consisting of glass and silicon.

5. The test apparatus of claim 2, wherein the ion exchange film consists of a Nafion film incorporating tetrathiafulvalene.

6. The test apparatus of claim 2, wherein the membrane is made of a material selected from the group consisting of cellulose acetate, polyvinyl alcohol, and polyurethane.

7. The test apparatus of claim 2, wherein the measuring apparatus includes means for maintaining each working electrode at 0 volts for 300 to 450 milliseconds and then pulsing each working electrode to a test voltage for 60 to 60 milliseconds, and for evaluating a test current during the last 10 milliseconds of the pulse.

8. The test apparatus of claim 2, wherein the enzyme is glucose oxidase, so that the sensing element is responsive only to glucose.

9. The test apparatus of claim 2, wherein the enzyme is a mixture of cholesterol oxidase, cholesterol esterase and horseradish peroxidase, so that the sensor is selective to total cholesterol.

10. The test apparatus of claim 2, further including a flow cell which receives the test device.

11. The test apparatus of claim 2, further including at least two counter electrodes made of a material selected from the group consisting of carbon, gold, and platinum, each counter electrode being supported by the bottom layer adjacent one of said working electrode/reference electrode pairs.

12. The test apparatus of claim 11, wherein at least one of the working and counter electrodes is made by screen printing conductive carbon ink onto the non-conducting bottom layer.

13. The test apparatus of claim 11, wherein at least one of the working and counter electrodes is made by screen printing a metallo-organic liquid onto a substrate made of a material selected from the group consisting of glass or ceramic, and then fired.

* * * * *